(12) United States Patent
Davis et al.

(10) Patent No.: US 6,880,933 B2
(45) Date of Patent: Apr. 19, 2005

(54) METHOD AND APPARATUS FOR MEASURING WAVEFRONT ABERRATIONS

(75) Inventors: Brett A. Davis, Cooparoo (AU); Michael J. Collins, Mt. Nebo (AU); Daoud R. Iskander, Hawthorne (AU); Jeffrey H. Roffman, Jacksonville, FL (US); Denwood F. Ross, III, Jacksonville, FL (US)

(73) Assignee: Johnson & Johnson Vision Cars, Inc., Jacksonville, FL (US)

( * ) Notice: Subject to any disclaimer, the term of this patent is extended or adjusted under 35 U.S.C. 154(b) by 0 days.

(21) Appl. No.: 10/606,389

(22) Filed: Jun. 26, 2003

(65) Prior Publication Data

US 2004/0004696 A1 Jan. 8, 2004

Related U.S. Application Data

(62) Division of application No. 09/677,191, filed on Oct. 2, 2000, now Pat. No. 6,616,279.

(51) Int. Cl.[7] .................................................. A61B 3/10
(52) U.S. Cl. ........................................................ 351/212
(58) Field of Search ............................. 351/211, 212, 351/246; 356/124, 124.5

(56) References Cited

U.S. PATENT DOCUMENTS

| 4,838,679 | A | 6/1989 | Bille |
| 5,062,702 | A | 11/1991 | Bille |
| 5,096,279 | A | 3/1992 | Hornbeck et al. |
| 5,624,437 | A | 4/1997 | Freeman et al. |
| 5,777,719 | A | 7/1998 | Williams et al. |
| 5,949,521 | A | 9/1999 | Williams et al. |
| 6,095,651 | A | 8/2000 | Williams et al. |
| 6,271,915 | B1 | 8/2001 | Frey et al. |
| 6,547,395 | B1 * | 4/2003 | Neal et al. .................. 351/246 |

FOREIGN PATENT DOCUMENTS

| WO | WO 98/27863 A1 | 7/1998 |
| WO | WO 99/27334 A1 | 6/1999 |
| WO | WO 00/10448 A1 | 3/2000 |

OTHER PUBLICATIONS

Dr. Williams and J. Liang; "Adaptive Optics for High Resolution Retinal Imaging"; Investigative Opththamology & Visual Science, Feb. 15, 1996, vol. 37, No. 3.

Walsh et al.; "Objective Technique for the Determination of Monochromatic Aberrations of the Human Eye"; Optical Society of America, Sep. 1984, vol. 1, No. 9, pp. 987–992.

W.N. Charman; "Wavefront Aberration of the Eye: A Review"; Optometry and Vision Science, vol. 68, No. 8, pp. 574–583.

(Continued)

*Primary Examiner*—George Manuel

(57) ABSTRACT

An apparatus and method for measuring wavefront aberrations. The apparatus comprises a reflecting device for reflecting selected portions of the wavefront, an imaging device for capturing information related to the selected portions, and a processor for calculating aberrations of the wavefront from the captured information. The method comprises reflecting selected portions of a wavefront onto the imaging device, capturing information related to the selected portions, and processing the captured information to derive the aberrations.

15 Claims, 7 Drawing Sheets

OTHER PUBLICATIONS

Junzhong Liang et al.; "Objective Measurement of Wave Aberrations of the Human Eye With the Use of a Hartmann Shack Wavefront Sensor"; Optical Society of America; Jul. 1994, vol. 11, No. 7.

Junzhong Liang et al.; "Effect of High Order Aberrations on Image Quality in the Human Eye"; Technical Digest Series, vol. 1, pp. 70–73.

Howard C. Howland et al.;"A Subject Method for the Measurement of Monochromatic Aberrations of the Eye"; J. Opt. Soc. Am, vol. 67, No. 11, Nov. 1977, pp. 1508–1518.

Bradford Howland et al.; "*Subjective Measurement of High–Order Aberrations of the Eye*"; *Science*, vol. 193, Feb. 1976, pp. 580–582.

G. Walsh et al.; "Objective Technique for the Determination of Monochromatic Aberrations of the Human Eye"; J. Opt. Soc. Am. Sep. 1984, vol. 1, No. 9, pp. 987–992.

Pablo Artal; "New Measurement of the Image Quality of the Human Eye by using an Optical Digital Method"; Trends in Optival Engineering, Mar. 1993.

Howard Howland; "Principles and Assumptions of Wavefront Sensing"; International Society for Contact Lens Research 10$^{th}$ Scientific Meeting, Phuket, Thailand.

* cited by examiner

METHOD AND APPARATUS FOR MEASURING WAVEFRONT ABERRATIONS

Divisional of prior application Ser. No. 09/677,191, filed Oct. 2, 2000, now U.S. Pat. No. 6,616,279.

FIELD OF THE INVENTION

The present invention relates generally to optical instruments and, more particularly, to a method and apparatus for measuring wavefront aberrations. The present invention is particularly useful, but not exclusively so, for measuring the optical wavefront in ophthalmic applications, e.g., measurement of aberrations of the eye, in corrective devices such as lenses (e.g., contact, spectacle, and intraocular), and for evaluating the ocular aberrations before, during and after refractive surgery to improve vision.

BACKGROUND OF THE INVENTION

The human eye is an optical system which employs a lens to focus light rays representing images onto the retina within the eye. The sharpness of the images produced on the retina is a factor in determining the visual acuity of the eye. Imperfections within the lens and other components and material within the eye, however, may cause the light rays to deviate from a desired path. These deviations, referred to as aberrations, result in blurred images and decreased visual acuity. Hence, a method and apparatus for measuring aberrations is desirable to aid in the correction of such problems.

One method of detecting aberrations introduced by an eye involves determining the aberrations of light rays exiting from within the eye. A beam of light directed into the eye as a point on the retina is reflected or scattered back out of the eye as a wavefront. The wavefront represents the direction of light rays exiting from the eye. By determining the propagation direction of individual portions of the wavefront, the aberrations introduced to the light rays passing through parts of the eye such as the cornea can be determined and corrected. In this type of system, increased accuracy in determining the aberrations can be achieved by reducing the size of the regions of the wavefront used to derive the propagation direction.

A general illustration of the generation of a wavefront is shown in FIG. 1. FIG. 1 is a schematic view of a wavefront 10 generated by reflecting a laser beam 12 off of the retina 20 of an eye 16. The laser beam 12 focuses to a small spot 14 on the retina 20. The retina 20, acting as a diffuse reflector, reflects the laser beam 12, resulting in a point source wavefront 10. Ideally, the wavefront 10 from a point source leaving a perfect eye would be represented by a spherical or planar wavefront 22. However, aberrations introduced by the eye 16 as the wavefront passes out of the eye result in an imperfect wavefront, as illustrated by the wavefront 10. The wavefront 10 represents aberrations which lead to defocus, astigmatism, spherical aberrations, coma, and other irregularities. Measuring and correcting these aberrations allow the eye 16 to approach its full potential, i.e., the limits of visual resolution.

FIG. 2 is an illustration of a prior art apparatus for measuring the wavefront 10 as illustrated in FIG. 1. By measuring the aberrations, corrective lens can be produced and/or corrective procedures performed to improve vision. In FIG. 2, a laser 22 generates the laser beam 12 which is routed to the eye 16 by a beam splitter 25. The laser beam 12 forms a spot 14 on the retina 20 of the eye 16. The retina reflects the light from the spot 14 to create a point source wavefront 10 which becomes aberrated as it passes through the lens and other components and material within the eye 16. The wavefront 10 passes through the beam splitter 25 toward a wavefront sensor 26. The apparatus described in FIG. 2 is commonly described as single-pass wavefront measurement system.

Typical prior art wavefront sensors 26 include either an aberroscope 30 and an imaging plane 28, as illustrated in FIG. 3, or a Hartmann-Shack sensor 40 and an imaging plane 28, as illustrated in FIG. 4. The wavefront sensor 26 samples the wavefront 10 by passing the wavefront 10 through the aberroscope 30 or the Hartmann-Shack sensor 40, resulting in the wavefront 10 producing an array of spots on an imaging plane 28. Generally, the imaging plane 28 is a charge coupled device (CCD) camera. By comparing an array of spots produced by a reference wavefront to the array of spots produced by the wavefront 10, the aberrations introduced by the eye 16 can be computed.

Each spot on the imaging plane 28 represents a portion of the wavefront 10, with smaller portions enabling the aberrations to be determined with greater precision. Thus, the smaller the sub-aperture spacing 32 and the size of the sub-aperture 33 in the aberroscope 30 of FIG. 3, and the smaller the lenslet sub-aperture spacing 42 in the Hartmann-Shack sensor 40 of FIG. 4, the more accurately the aberrations can be determined.

An example of a Hartmann-Shack system is described in U.S. Pat. No. 6,095,651 to Williams et al., entitled Method and Apparatus for Improving Vision and the Resolution of Retinal Images, filed on Jul. 2, 1999, incorporated herein by reference.

The resolution of the aberrations in such prior art devices, however, is limited by the grid size 32 and aperture size 33 in an aberroscope 30 (see FIG. 3), and by the lenslet sub-aperture spacing 42 in a Hartmann-Shack sensor 40 (see FIG. 4). Due to foldover, reductions to grid size 32 and lenslet sub-aperture spacing 42 are limited. Foldover occurs in an aberroscope sensor 30, for example, when two or more spots 31A, 31B, and 31C on imaging plane 28 overlap thereby leading to confusion between adjacent sub-aperture spots. Similarly, foldover occurs in Hartmann-Shack sensors 40 when two or more spots 41A, 41B, 41C, and 41D on imaging plane 28 overlap. Foldover may result from a grid size 32 or lenslet sub-aperture spacing 42 which is too small, a high degree of aberration, or a combination of these conditions. Hence, the grid size 32 or lenslet sub-aperture spacing 42 must be balanced to achieve good spatial resolution while enabling the measurement of large aberrations. Accordingly, the ability to measure a high degree of aberration comes at the expense of spatial resolution and vice versa.

The constraints imposed by the aberroscope and Hartmann-Shack approaches limit the effectiveness of these systems for measuring large aberrations with a high degree of spatial resolution. These limitations prevent optical systems with large aberrations from being measured, thereby preventing them from achieving their full potential. Accordingly, ophthalmic devices and methods which can measure a wide range of aberrations with a high degree of spatial resolution would be useful.

SUMMARY OF THE INVENTION

The present invention discloses an apparatus and method for determining the aberrations of a wavefront with a high degree of accuracy. The apparatus includes a plurality of mirrors for reflecting selected portions of the wavefront, an imaging device for capturing information related to the selected portions, and a processor for controlling the plurality of mirrors and interpreting the captured information to compute the aberrations. The method includes reflecting selected portions of a wavefront onto an imaging device, capturing information related to the selected portions, and processing the captured information to derive the aberrations. The apparatus and method of the present invention are capable of measuring a wide range of aberrations with a high degree of spatial resolution.

The wavefront originates as a point source within a focusing optical system (e.g. the eye). The point source is generated by directing a beam of radiation (e.g., a laser) through the focusing optical system and scattering or reflecting the beam. A beam splitter disposed in the path of the laser beam directs the laser beam through the focusing optical system. The focusing optical system has an interior portion functioning as a diffuse reflector for reflecting or scattering the beam. The wavefront resulting from the point source passes through the focusing optical system and the beam splitter to the wavefront sensor of the present invention. The wavefront sensor measures distortions of the wavefront as an estimate of aberrations introduced by the focusing optical system. Aberrations are then computed by a processor coupled to the wavefront sensor.

DETAILED DESCRIPTION OF THE INVENTION

Figure 1:
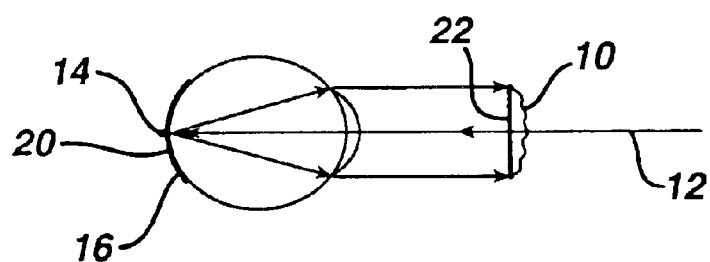
FIG. 1 is a schematic of a wave produced by a laser beam reflected by the retina of an eye.
Figure 2:
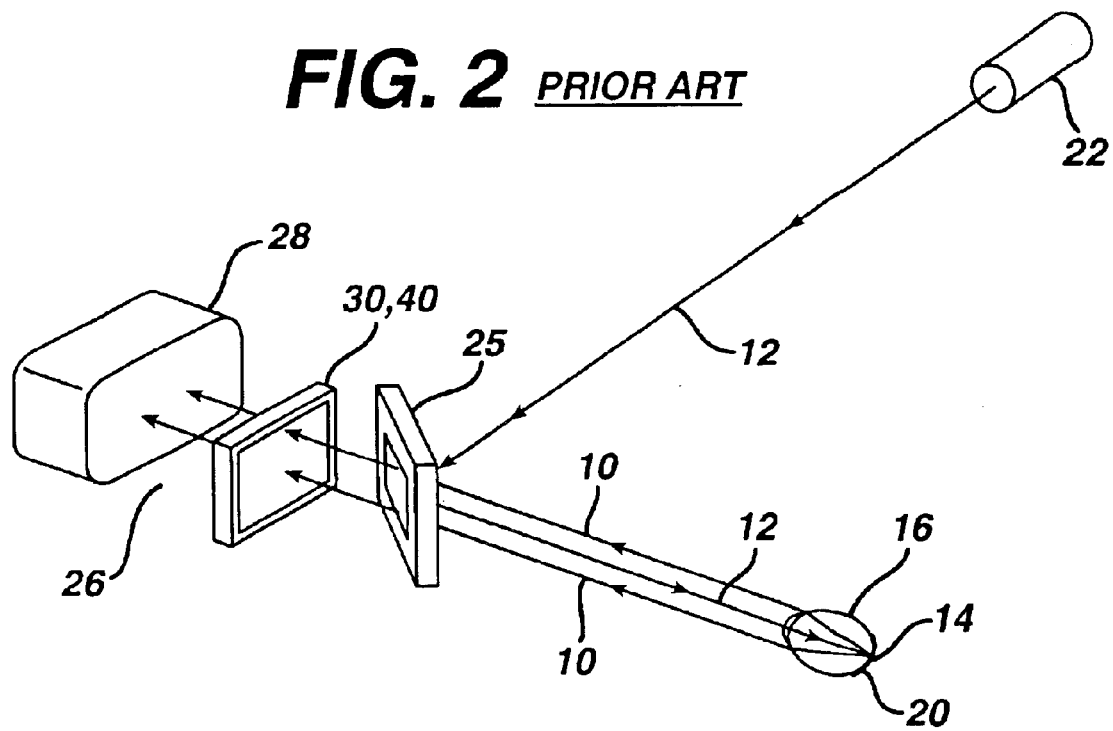
FIG. 2 is a schematic of a prior art apparatus for measuring aberrations introduced by an eye.
Figure 3:
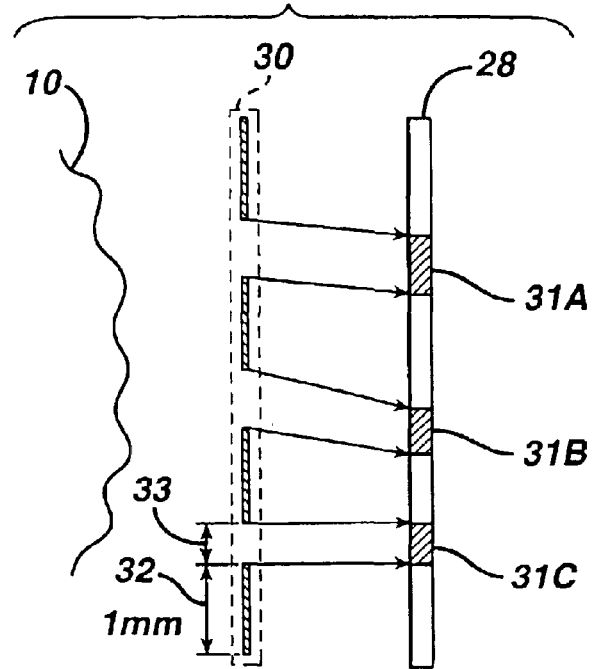
FIG. 3 is a schematic of an aberroscope for use in a prior art apparatus for measuring aberrations.
Figure 4:
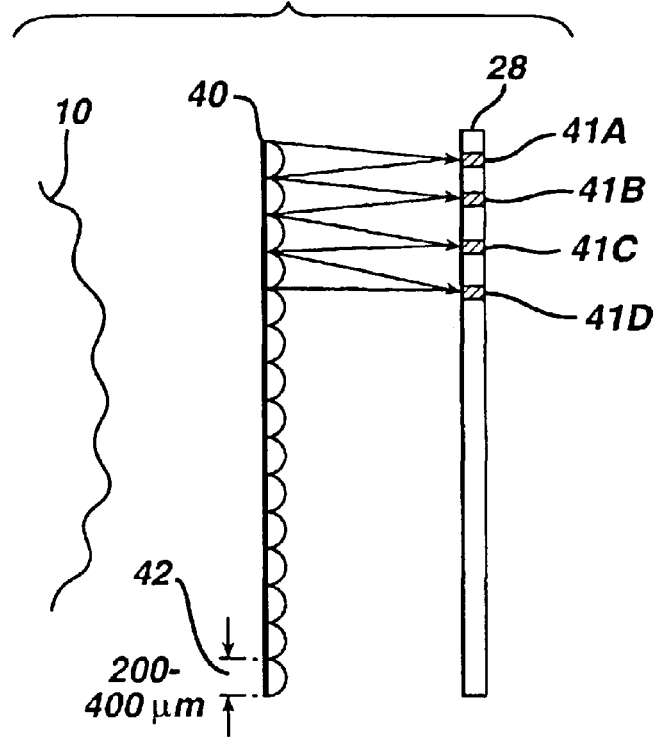
FIG. 4 is a schematic of a Hartmann-Shack lenslet array for use in a prior art apparatus for measuring aberrations.
Figure 5:
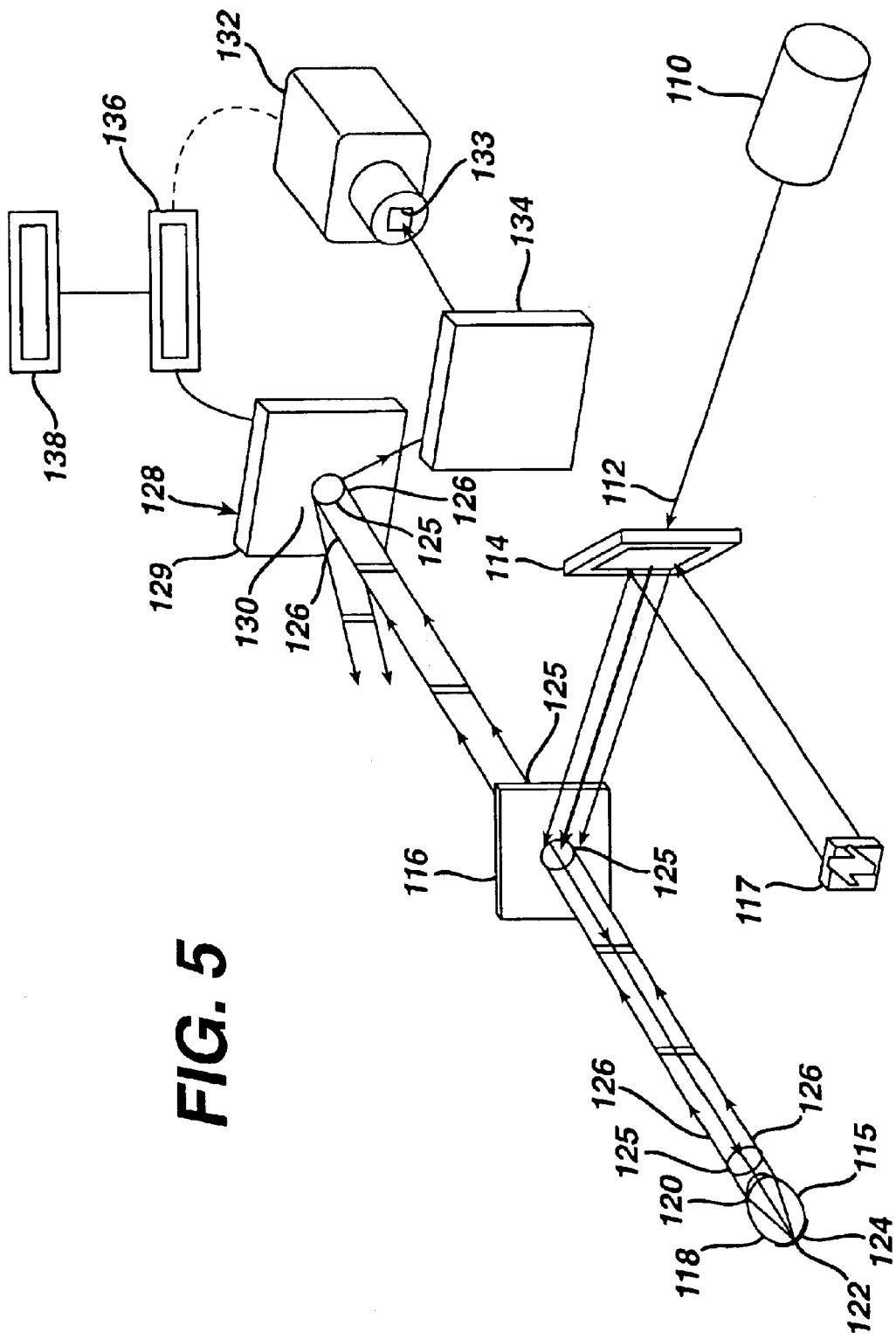
FIG. 5 is a schematic of an apparatus for measuring aberrations introduced by an optical system in accordance with the present invention.

Illustrated in FIG. 5 is a preferred embodiment of a wavefront measuring device 100 in accordance with the present invention. In a general overview of the device 100 illustrated in FIG. 5, a radiation source 110 generates a beam 112. The beam 112 passes through an optional beam splitter 114 unaltered. Another beam splitter 116 then redirects the beam 112 toward an optical system 115, e.g., an eye 118. The beam 112 enters the eye 118 through the cornea 120 where it is reflected by the retina 124 to produce a point source image wavefront 126 that travels back out of the eye 118. The wavefront 126 is affected by defects within the eye 118 which cause the aberrations. The affected wavefront 126 passes through the beam splitter 116 toward a reflection device 128. Individual mirror regions 130 within the reflection device 128 selectively reflect portions of the wavefront 126 toward an imaging device 132, via a redirecting mirror 134, which captures information related to the wavefront 126. A processor 136 is used to control the reflection device 130 and to process the captured information.

The radiation source 110 is a device capable of generating a focused beam of photons, and is preferably a laser. Alternative radiation sources 110 include a laser diode, super-luminescent diode, or essentially any suitable radiation device. Additionally, the radiation source 110 may include a spacial filter for correcting noise associated with the radiation source 110.

The optional beam splitter 114 is a device capable of selectively passing and directing beams within the wavefront measuring device 100. In the preferred embodiment, the optional beam splitter 114 is configured to pass light generated by the radiation source 110 and to reflect light from the fixation target 117. This configuration allows light from the fixation target 117 to be placed in the same path as light from the radiation source 110 that is heading toward the eye 118. The fixation target 117 is an optional component which provides a focusing point for the person whose eye 118 is being scanned, thereby controlling eye movements and accommodation (focusing). The optional beam splitter 114 can be removed if the fixation target 117 is not used. Preferably, the optional beam splitter 114 is a polarizing beam splitter which selectively passes or reflects light based on the polarization of the light.

The other beam splitter 116 is also capable of selectively passing and directing beams. The beam splitter 116 is configured to reflect the beam 112 and light from the fixation target 117 toward the optical system 115, e.g., the eye 118, and to pass the light projecting from the optical system 115 unaltered. Preferably, the beam splitter 116 is also a polarizing beam splitter as discussed above.

The illustrated optical system 115 is the eye 118. Alternatively, the optical system may include a reflective surface and a contact lens or eyeglass, an eye and a contact lens or eyeglass, a telescope, a microscope, or other type of optical system. Here, the beam 112 from the radiation source 110 is kept much smaller than the diffraction limited pupil aperture (approx. 2 mm) in order to form a spot 122 on the retina 124. A focusing lens may also be used in the path of the beam 112 to account for defocus and/or astigmatism of the eye. The retina 124, acting as a diffuse reflector, effectively becomes the source for light leaving the eye 118, thereby creating the wavefront 126. As the light is reflected off of the retina 124, aberrations due to imperfections within the eye are introduced. Since the beam 112 is small, aberration producing imperfections within the eye 118 have little effect as the beam enters the eye 118. Therefore, the aberrations are introduced to the light primarily upon exiting the eye 118, essentially making this a single pass aberration measurement system. Single pass measurement systems are desirable since double pass measurement systems effectively count aberrations twice, e.g., aberrations are introduced to light entering the eye 118, and introduced again as the light leaves the eye 118.

One or more optical devices, such as lenses 125, are positioned between the eye 118 and the reflection device 128. The lenses 125 transfer the point source image wavefront 126 between the eye 118 and the reflection device 128 such that the propagation directions of the waves which make up the wavefront 126 are preserved as they are passed from the eye 118 to the reflection device 128. Optical devices such as the lenses 125 used in the present invention are well known to those in the art.

Figure 5A:
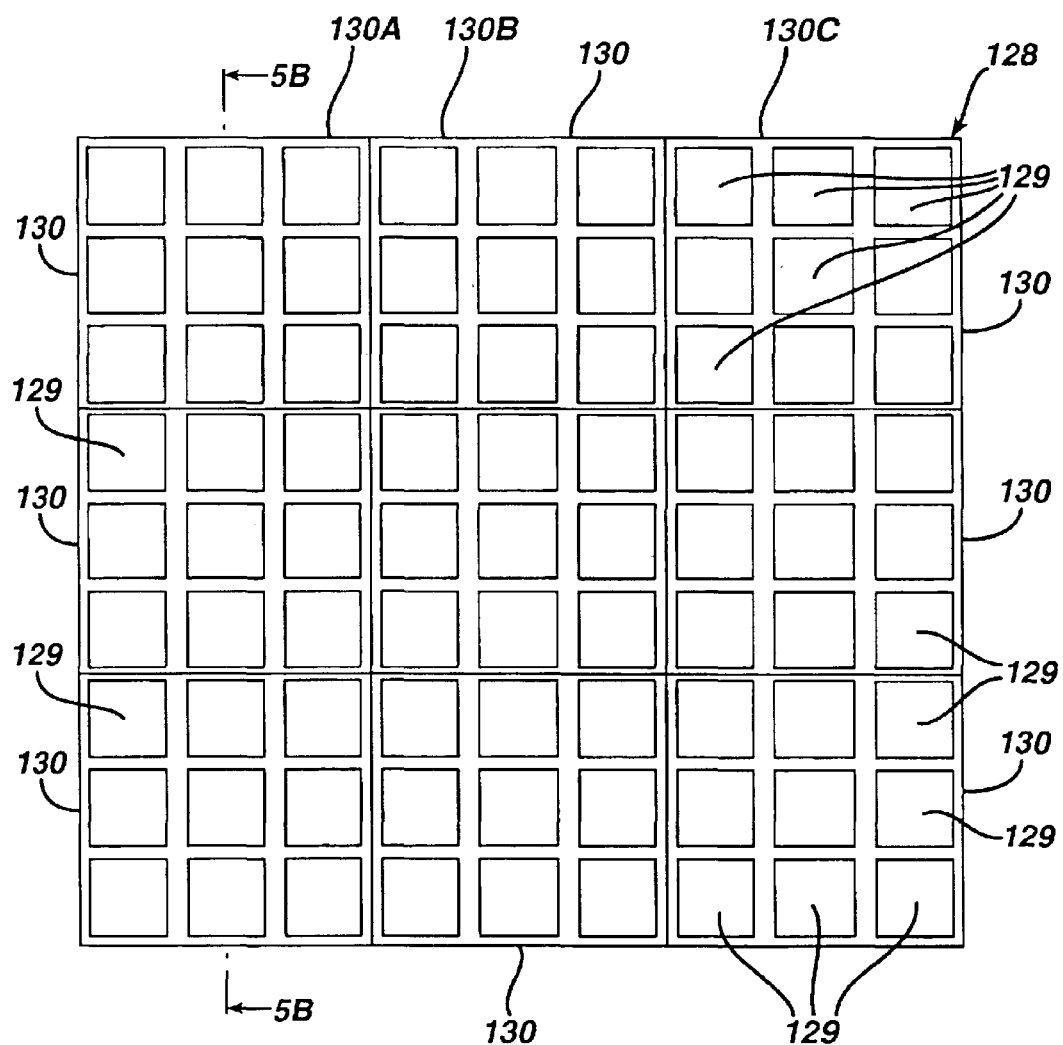
FIG. 5A is an illustrative schematic of a reflection device in accordance with the present invention.
Figure 5B:
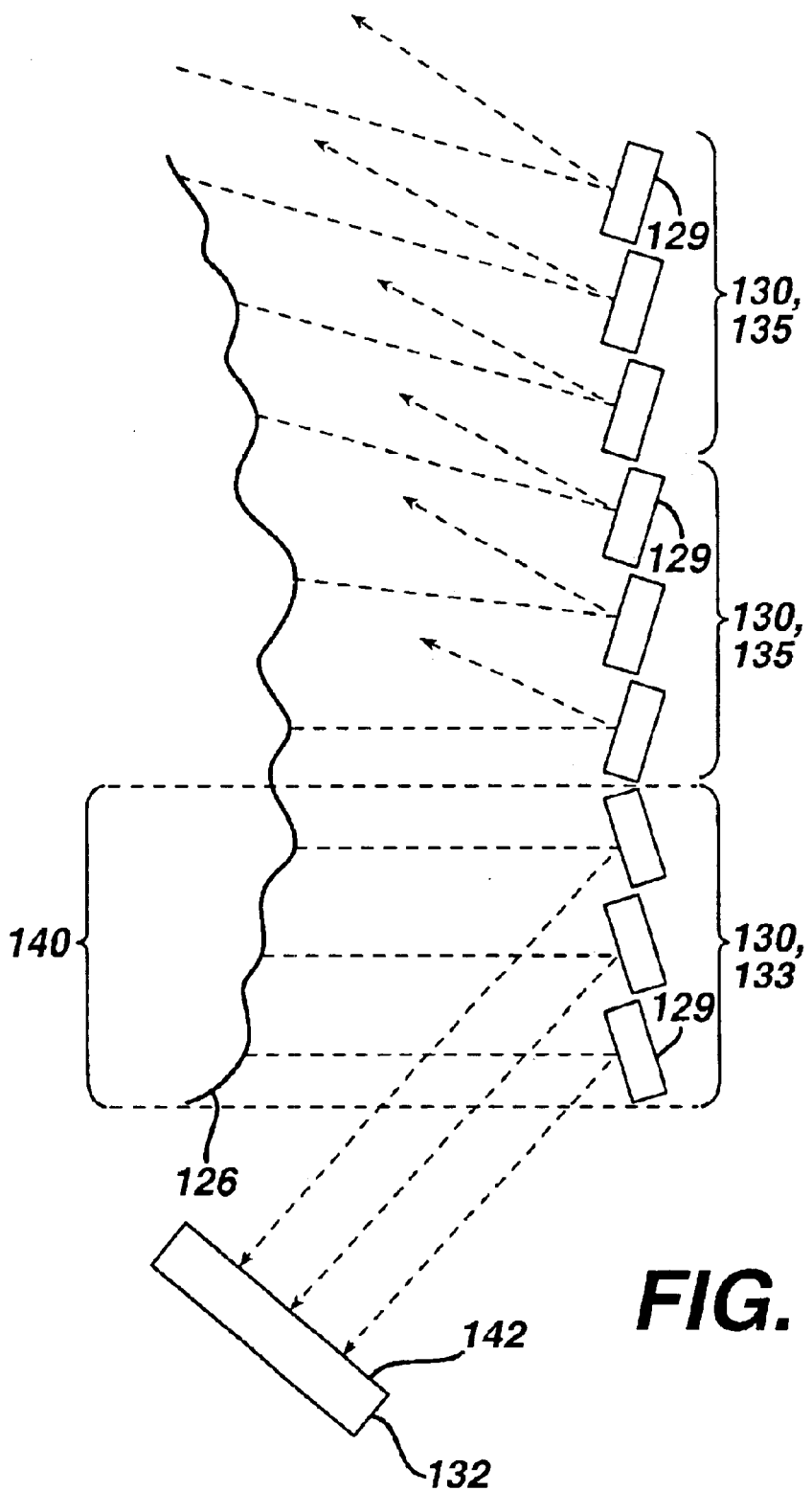
FIG. 5B is a cross sectional view of the reflection device of FIG. 5A including a wavefront and an imaging device in accordance with the present invention.

The reflection device 128 has a plurality of mirrors 129 which form or can be grouped to form mirror regions 130 (see FIGS. 5 and 5A). Each mirror region 130 is capable of reflecting a portion of the wavefront 126 for measurement of that portion independent of the other portions (see FIG. 5B). Preferably, each mirror region 130 may be oriented in at least two positions. In a first position 133 (FIG. 5B), a mirror region 130 will reflect a portion 140 of the wavefront 126 incident on the mirror region 130 in a direction to be received by the imaging device 132 and, in a second position 135, the mirror regions 130 will reflect the portions of the wavefront 126 in a direction away from the imaging device 132.

Each mirror region 130 may be formed of a single mirror 129, or multiple mirrors 129 which are preferably adjacent to one another as illustrated in FIG. 5A. For example, if the reflection device 128 includes an array of 1000 mirrors by 1000 mirrors, each mirror region 130 may include a single mirror 129, an array of 3 mirrors by 3 mirrors as illustrated in FIG. 5A, an array of 100 mirrors by 100 mirrors, or any other suitable grouping. While the present embodiment contemplates that each mirror region 130 would have the same configuration of mirrors, such in not believed necessary.

Figure 6:
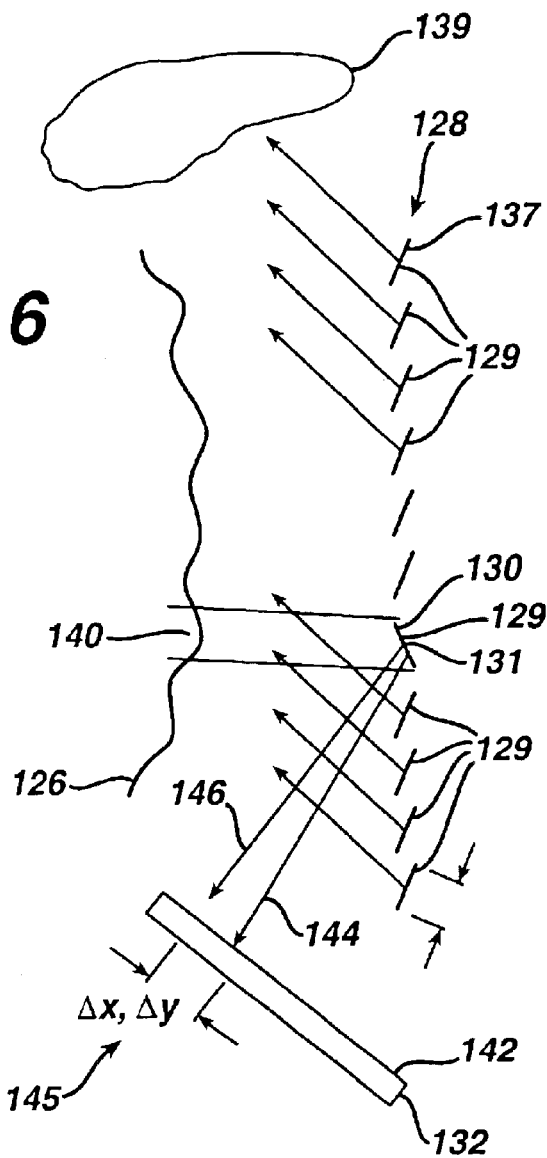
FIG. 6 is a schematic illustrating the reflection of a portion of a wavefront in accordance with the present invention.

FIG. 6 illustrates the reflection of a portion 140 of the wavefront 126 by a mirror region 130 within a reflection device 128 toward an imaging device 132 to determine an aberration. Here the mirror region 130 has a single mirror 129. When a mirror 129 such as mirror 131 is in the first position 133 (see FIG. 5B), the wavefront portion 140 is directed toward an imaging plane 142 of the imaging device 132 as a reflected wavefront portion 144. The other mirrors 129 such as the mirror 137 in the second position 135 (see FIG. 5B) reflect the portion of the wavefront 126 incident thereon away from imaging plane 142, such as to area 139.

To capture the entire wavefront 126, each of the mirrors 129 or group of mirrors 130, are in turn positioned to reflect the respective portion of the wavefront incident thereon towards the imaging device 132, and then repositioned to reflect away as another mirror 129 is positioned to reflect towards the imaging device 132. Of course if a mirror region 130 has more than one mirror 129, then preferably, all mirrors 129 of each mirror region 130 are positioned as a unit.

Aberrations within the wavefront portion 140 displace the reflected wavefront portion 144 from an aberration free path 146 by an amount proportional to the local slope of the wavefront portion 140 corresponding to the mirror 131. Given the displacement 145 between the location of reflected wavefront portion 144 and aberration free path 146 incident on imaging plane 142 and the distance from the wavefront portion 140 to the imaging plane 142, the propagation direction of the wavefront portion 140 can be computed using a known method such as an inverse tangential function, i.e., the ratio of the length of the side opposite the angle of the wavefront portion 140 to the length of the side adjacent to the angle. The aberrations of the wavefront portion 140 can then be calculated using known methods.

In the preferred embodiment, each mirror region 130 is individually oriented to direct a corresponding portion of the wavefront 126 toward the imaging device 132 where information related to that portion is captured by the imaging device 132. Alternatively, more than one of the mirror regions 130 may be oriented to direct respective portions of the wavefront 126 toward the imaging device 132 substantially simultaneously. If more than one of the mirror regions 130 direct simultaneously respective portions of the wavefront 126 toward the imaging device 132, such mirror regions 130 should be separated by another region of mirrors which reflect away from the imaging device 132 to prevent foldover between the imaged regions. For example, referring to FIG. 5A, if two mirror regions 130A and 130C are oriented substantially simultaneously to direct respective portions of the wavefront 126 toward the imaging device 132, the two mirror regions 130A and 130C will be separated by one or more mirror regions 130 such as a third mirror region 130B which will be oriented to reflect a respective portion of the wavefront 126 away from the imaging device 132. By varying the size of the mirror regions 130, and the number of mirror regions 130 that simultaneously direct portions of the wavefront 126 toward the imaging device 132, the speed required to capture all of the wavefront 126 and the spatial resolution of the system can be adjusted.

One preferable reflection device 128 is a Digital Micromirror Device™ (DMD™). It will be apparent to those in the art that other types of reflecting devices may be used in accordance with the present invention. DMDs™ are described in U.S. Pat. No. 5,096,279 to Hornbeck et al., entitled "Spatial Light Modulator and Method," and in U.S. Pat. No. 4,954,789 to Sampsell, entitled "Spatial Light Modulator," both of which are incorporated herein by reference.

Figure 7:
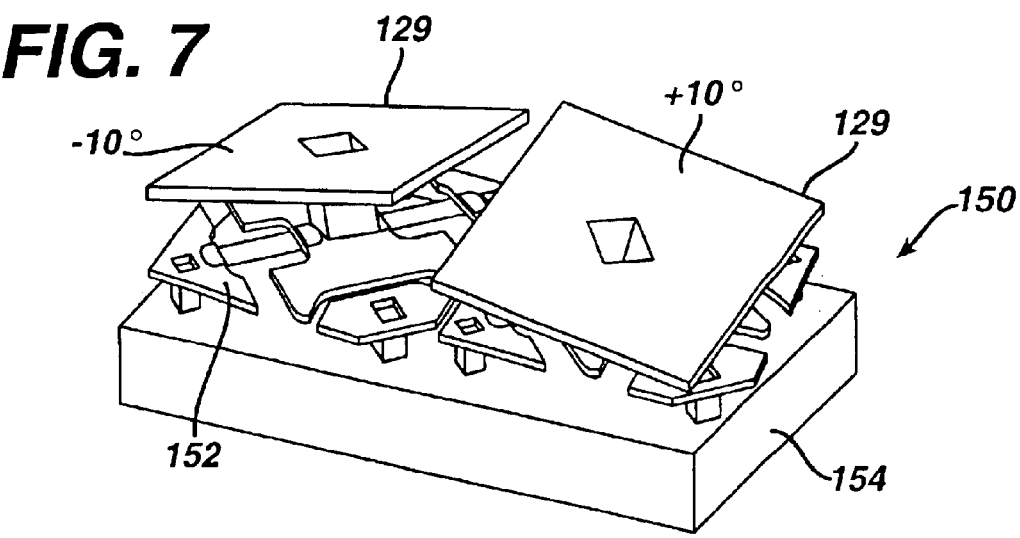
FIG. 7 is an perspective view of a portion of a Digital Micromirror Device™ (DMD™)

FIG. 7 depicts a portion of a Digital Micromirror Device™ (DMD™) 150. A DMD™ includes an array of hundreds or thousands of tiny tiltable mirrors 129, each of which is capable of reflecting a portion of the wavefront 126. FIG. 7 depicts two individual mirrors 129 within the DMD™ 150. To permit the mirrors to tilt, each mirror 129 is attached to one or more hinges 152 mounted on support posts, and spaced by means of a fluidic (air or liquid) gap over underlying control circuitry on a CMOS substrate 154. The control circuitry provides electrostatic forces, which cause each mirror 129 to selectively tilt. In operation, data is loaded to memory cells of the DMD™ 150 and, in accordance with this data, individual mirrors 129 are tilted so as to either reflect light towards or away from the imaging device 132 via the redirecting mirror 134 as seen in FIG. 5. Suitable DMD™ devices include SXGA and SVGA DMD™ devices available from Texas Instruments.

Figure 8:
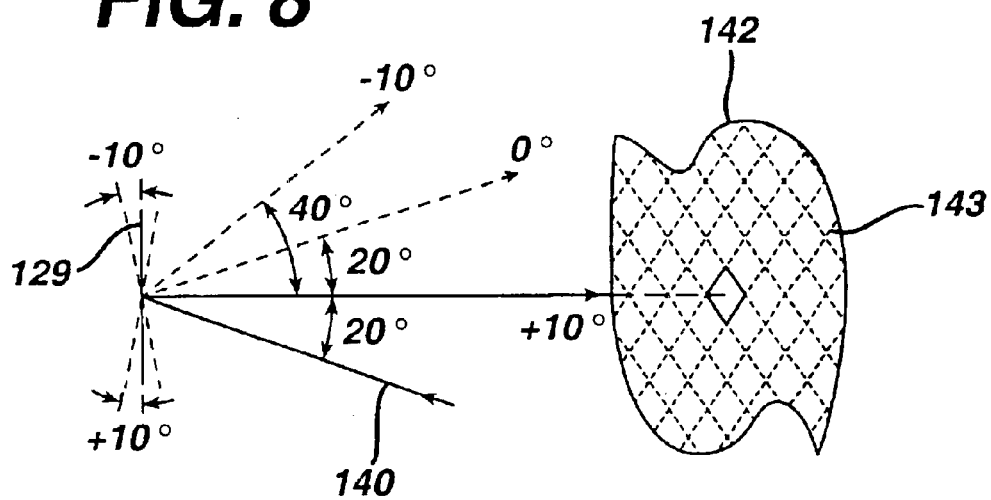
FIG. 8 is a schematic illustrating the reflection of a portion of a wavefront by a single mirror within the DMD™ of FIG. 7 in accordance with the present invention.

FIG. 8 depicts in detail the reflection of the wavefront portion 140 (FIG. 6) by a mirror 129 of a DMD™. The individual mirror 129 has three positions (i.e., −10°, 0°, +10°). In the +10° position, representing the first position 133 of FIG. 5B, the wavefront portion 140 is directed toward the imaging plane 142. In the 0° and −10° positions, either representing the second position 135 of FIG. 5B, the wavefront portion 140 is directed away from the imaging plane 142. Preferably, the imaging plane 142 includes a plurality of cells 143 capable of detecting energy from the wavefront portion 140. Although each mirror of a DMD™ has three positions, only two are needed in the present invention.

In the illustrated embodiment, the wavefront portions 140 are directed toward the imaging device 132 via a redirecting mirror 134. The redirecting mirror 134 is optically positioned (not necessarily physically positioned) between the reflection device 128 and the imaging device 132 to reflect the wavefront portions 140 from the mirror regions 130 to the imaging device 132. This facilitates the placement of the imaging device 132 in relation to the plurality of mirrors 128. Alternatively, the wavefront portions could pass directly from the reflection device 128 to the imaging device 132, thereby eliminating the need for the redirecting mirror 134.

Figure 9:
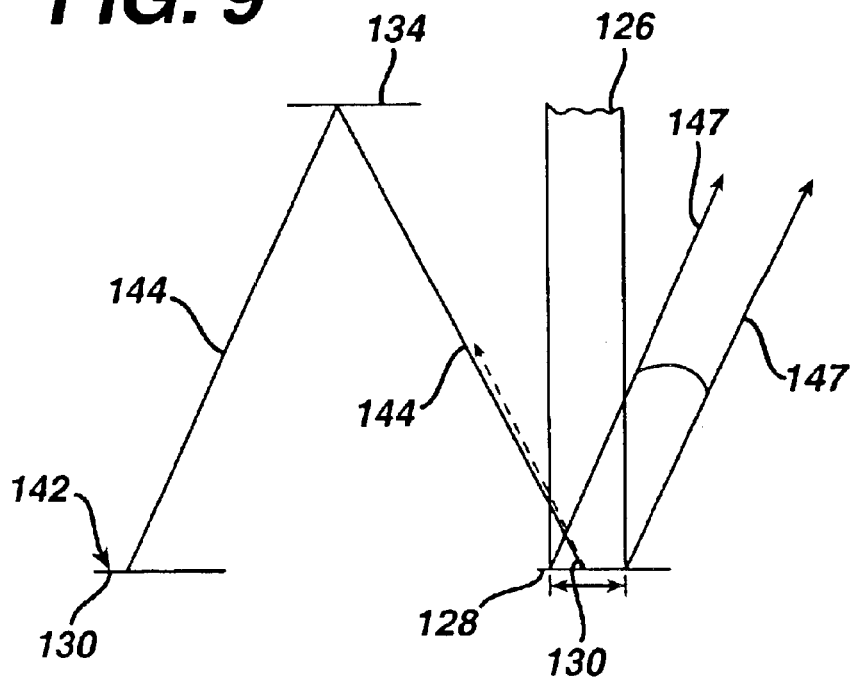
FIG. 9 is a schematic illustrating the reflection and redirection of a portion of a wavefront onto an imaging device in accordance with the present invention.

FIG. 9 depicts in detail the operation of redirecting mirror 134 as seen in FIG. 5. In FIG. 9, the reflection of a wavefront portion 144 is isolated from the entire wavefront 126 by the mirror region 130 within the reflection device 128. The reflection of the wavefront portion 144 is reflected off of a redirecting mirror 134 onto the imaging plane 142 of the imaging device 132. The unmeasured portions 147 of the wavefront 126 are directed away from the imaging plane 142. The redirecting mirror 134 facilitates the placement of the imaging device 132 in relation to the reflection device 128 by adding flexibility. The flexibility is due to the ability to position the imaging device 132 in a location other than in the direct line of sight the reflection device 128.

The imaging device 132 is capable of precisely detecting the location of energy incident to an imaging plane 133. Preferably, the imaging device 132 is a charge coupled device (CCD) camera. A charge coupled camera is a device capable of converting energy incident to an imaging plane 133 into a digital representation. Charge coupled devices are well known and a suitable device for use with the present invention would be readily apparent to those skilled in the art.

The processor 136 controls the orientation of the mirror regions 130. In addition, the processor 136 receives information from the imaging device 132 and analyzes the information to compute the aberrations. The information may be stored in a storage register prior to processing by processor 136 or may be processed immediately. In the preferred embodiment, the processor 136 orients the individual mirror regions 130 (all the mirrors 129 of the mirror region 130) to reflect towards the imaging device 128 at different times for computing the aberrations of the wavefront 126. In an alternative embodiment, the processor 136 substantially simultaneously orients two or more mirror regions toward the imaging device 132 to compute the aberrations of the wavefront 126. In this alternative embodiment, the individual mirror regions 130 are separated by a buffer mirror region reflecting away from the imaging device 132 to prevent foldover between portions of the wavefront 126 corresponding to the individual mirror regions 130 as previously discussed. It is apparent to those skilled in the art that the control of the plurality of mirrors 128, the receipt of information from the imaging device 132, and the processing of information may be performed by a single processor or divided among a plurality of processors.

In accordance with an embodiment of the present invention, the aberration correction device 138 is coupled to the processor 136. Alternatively, information calculated by the processor 136 may be stored on a hard drive, diskette, server, compact disc, digital versatile disc, or essentially any device capable of storing information. The stored information is then passed to an aberration correction device 138. The aberration correction device 138 includes a known lens grinder, contact lens manufacturing system, surgical laser system, or other optical system correction device. In a surgical laser system, a laser can be optically positioned relative to the beam splitter 116 to direct a laser cutting beam toward the cornea 120 of the eye 118, in a manner well known in the art, for the purpose of performing ophthalmic surgery.

For illustrative purposes, the present invention has been described in terms of measuring wavefront aberrations introduced by a human eye. However, it will be readily apparent to those skilled in the art that the present invention can be used to measure aberrations created by other optical systems, e.g. eyeglasses, telescopes, binoculars, monoculars, contact lenses, non-human eyes, or combination of these systems.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A sensor for measuring a wavefront, said sensor comprising:
   a plurality of mirrors for receiving the wavefront, said plurality of mirrors comprising a first mirror region for reflecting a first portion of the wavefront, said first mirror region having a first position to reflect in one direction and a second position to reflect in another direction;
   an imaging device for detecting said first portion of the wavefront, said first mirror region directing said portion of the wavefront to be received by said imaging device when said first mirror region is in said first position, said first mirror region directing said portion of the wavefront so as not to be received by said imaging device when said first mirror region is in said second position; and
   a processor for controlling the movement of said first mirror region between said first and second positions.

2. A sensor in accordance with claim 1, wherein said plurality of mirrors further comprises a second mirror region for reflecting a second portion of the wavefront, said second mirror region having a first position and a second position; said second mirror region directing said second portion of the wavefront to be received by said imaging device when said second mirror region is in said first position, said second mirror region directing said second portion of the wavefront so as no to be received by said imaging device when said second mirror region is in said second position; and said processor controlling the movement of said second mirror region between said first and second positions.

3. A sensor in accordance with claim 2 wherein said first mirror region and saidsecond mirror region each comprise at least one mirror.

4. A sensor in accordance with claim 2 wherein said processor is capable of receiving information from said imaging device for computing a first wave aberration for said first portion of the wavefront and a second wave aberration for said second portion of the wavefront.

5. A sensor in accordance with claim 4, wherein said processor is capable of positioning substantially simultaneously said first mirror region in said first position and said second mirror region in said first position, and computes said first and second wave aberration for said first and second portions of the wavefront.

6. A sensor in accordance with claim 4, wherein said processor positions said first mirror region in said first position and said second mirror region in said first position at different times for computing said first wave aberration and said second wave aberration for said first and second positions of the wavefront.

7. A sensor in accordance with claim 2, wherein said first mirror region and said second mirror region are separated by a third mirror region for reflecting a third portion of the wavefront, said third mirror region having a first position wherein said third portion of the wavefront is directed to said imaging device and a second position wherein said third portion of the wavefront is directed so as not to be received by said imaging device.

8. A sensor in accordance with claim 7, wherein said third mirror region is in said second position when said first and second mirror regions are in said first position.

9. A sensor in accordance with claim 1 wherein said plurality of mirrors is provided by a digital micromirror device.

10. A sensor in accordance with claim 1 wherein said imaging device is a charge coupled device.

11. A sensor in accordance with claim 1, further comprising: a redirecting mirror optically positioned between said reflecting device and said imaging device for reflecting said first portion of the wavefront from said reflecting device to said imaging device.

12. An apparatus for measuring aberrations of a point source image wavefront emitted from a focusing optical system, comprising:
 a radiation source for generating a beam to be directed to the focusing optical system;
 a plurality of mirror for receiving the point source image wavefront from the focusing optical system, said plurality of mirrors comprising a first mirror region for reflecting a first portion of the point source image wavefront, said first mirror region having a first position and a second position;
 an imaging device for receiving said first portion of the point source image wavefront, said first mirror region when in said first position directing said portion of the point source image wavefront to be received by said imaging device, said first mirror region when in said second position directing said portion of the point source image wavefront so as not to be received by said imaging device; and
 a processor for controlling the movement of said first mirror region between said first and second positions.

13. An apparatus in accordance with claim 12, wherein said plurality of mirrors further comprises a second mirror region for reflecting a second portion of the point source image wavefront, said second mirror having a first position and a second position; said first position of said second mirror region directing said second portion of the point source image wavefront to be received by said imaging device, said second position of said second mirror region directing said second portion of the point source image wavefront so as not to be received by said imaging device; and said processor controlling the movement of said second mirror region between said first and second positions.

14. An apparatus in accordance with claim 12, further comprising:
 a redirecting mirror optically positioned between said reflecting device and said imaging device for facilitating the placement of said imaging device in relation to said reflecting device.

15. An apparatus in accordance with claim 12, further comprising:
 a fixation target; and
 a beam splitter optically positioned between said radiation source and the focusing system for optically combining said fixation target with said beam.

* * * * *